United States Patent
Wong et al.

(10) Patent No.: US 10,052,290 B2
(45) Date of Patent: Aug. 21, 2018

(54) ENTERIC-COATED HEMOGLOBIN MULTIPARTICULATE FOR ORAL DELIVERY OF HEMOGLOBIN BASED OXYGEN CARRIERS

(71) Applicant: Billion King International Ltd., Hong Kong (HK)

(72) Inventors: Bing Lou Wong, Irvine, CA (US); Sui Yi Kwok, Hong Kong (HK)

(73) Assignee: Billion King International Ltd., Hong Kong (HK)

( * ) Notice: Subject to any disclaimer, the term of this patent is extended or adjusted under 35 U.S.C. 154(b) by 0 days.

(21) Appl. No.: 15/016,224

(22) Filed: Feb. 4, 2016

(65) Prior Publication Data

US 2017/0224626 A1    Aug. 10, 2017

(51) Int. Cl.
| | |
|---|---|
| A61K 9/50 | (2006.01) |
| A61K 45/06 | (2006.01) |
| A61K 38/42 | (2006.01) |
| A61K 47/18 | (2017.01) |
| A61K 47/20 | (2006.01) |
| A61K 47/40 | (2006.01) |

(52) U.S. Cl.
CPC .......... *A61K 9/5078* (2013.01); *A61K 9/5026* (2013.01); *A61K 38/42* (2013.01); *A61K 45/06* (2013.01); *A61K 47/40* (2013.01)

(58) Field of Classification Search
CPC .. A61K 5/5073; A61K 9/5026; A61K 9/5042; A61K 31/045; A61K 9/0053; A61K 9/50; A61K 9/5089; A61K 31/205; A61K 31/225; A61K 9/5031; A61K 31/4045; A61K 31/405; A61K 9/5078; A61K 9/501; A61K 47/183; A61K 45/06; A61K 47/26; A61K 47/20; A61K 9/5015; A61K 9/5047; A61K 38/42; A61K 47/40
See application file for complete search history.

(56) References Cited

U.S. PATENT DOCUMENTS

| | | | |
|---|---|---|---|
| 2,799,241 A | 7/1957 | Wurster | |
| 5,929,031 A * | 7/1999 | Kerwin | C07K 14/805 514/13.4 |
| 6,399,116 B1 | 6/2002 | Xiu | |
| 7,932,356 B1 | 4/2011 | Wong et al. | |
| 7,989,593 B1 | 8/2011 | Wong et al. | |
| 8,048,856 B1 | 11/2011 | Wong et al. | |
| 8,084,581 B1 | 12/2011 | Wong et al. | |
| 8,106,011 B1 | 1/2012 | Wong et al. | |
| 9,066,933 B2 | 6/2015 | Wong et al. | |
| 9,763,889 B2 | 9/2017 | Wong et al. | |
| 2009/0117207 A1 * | 5/2009 | Zoltani | A61K 31/138 424/699 |
| 2013/0059000 A1 * | 3/2013 | Wong | A61K 38/42 424/456 |

OTHER PUBLICATIONS

Gupta (Journal of Controlled Release (Dec. 10, 2013) 172(2): 541-549).*
Shaji et al (Indian J Pharm Sci (2008) 70(3):269-77).*
Artursson, P., et al. "Effect of chitosan on the permeability of monolayers of intestinal epithelial cells (Caco-2)." Pharm Res., 1994, 11: 1358-1361.
Ballard, T.S., et al. "Regulation of tight-junction permeability during nutrient absorption across the intestinal epithelium." Annu. Rev. Nutr, 1995, 15: 35-55.
Barnikol, W.K., et al. "Complete healing of chronic wounds of a lower leg with haemoglobin spray and regeneration of an accompanying severe dermatoliposclerosis with intermittent normobaric oxygen inhalation (INBOI): a case report." Ger Med Sci., 2011, 9 (DOI: 10.3205/000131).
Barrett, K.E., et al. "New Delhi: Tata-McGraw-Hill." Ganong's Review of Medical Physiology, 2009, 23rd edition, pp. 619-620.
Bonaventura, C., et al. "Allosteric effects on oxidative and nitrosative reactions of cell-free hemoglobin." IUBMB Life, 2007, 59(8-9): 498-505.
Brunel, F., et al. "Self-assemblies on chitosan nanohydrogels." Macromol Biosci., 2010, 10(4): 424-432.
Cicco, G., et al. "Wound healing in diabetes: hemorheological and microcirculatory aspects." Adv Exp Med Biol. 2011, 701: 263-269.
Dünnhaupt, et al. "Distribution of thiolated mucoadhesive nanoparticles on intestinal mucosa." International Journal of Pharmaceutics, 2011, 408 (1-2): 191-199.
Hackett, P.H., et al. "Dexamethasone for prevention and treatment of acute mountain sickness." Aviat space Environ Med., 1988, 59: 950-954.
Hiromi, Sakai, et al. "Review of Hemoglobin-Vesicles as Artificial Oxygen Carriers." Artificial organs, 2009, 33(2): 139-145.
Iwasaki, N, et al. "Feasibility of polysaccharide hybrid materials for scaffolds in cartilage tissue engineering: evaluation of chondrocyte adhesion to polyion complex fibers prepared from alginate and chitosan." Biomacromolecules, 2004, 5 (3): 828-833.
Levien, L.J. "South Africa: clinical experience with Hemopure." ISBT Science Series, 2006, 1(1): 167-173.
Lin, Y.H., et al. "Multi-ion-crosslinked nanoparticles with pH-responsive characteristics for oral delivery of protein drugs." J Control Release., 2008: 132(2), 141-149.

(Continued)

*Primary Examiner* — Snigdha Maewall
(74) *Attorney, Agent, or Firm* — Idea Intellectual Limited; Margaret A. Burke; Sam T. Yip

(57) ABSTRACT

The present invention provides an enteric-coated hemoglobin multiparticulate comprising a core, a hemoglobin formulation coating, an inner or sub-coating, and an enteric coating. The present invention also provides a method of preparing said enteric-coated hemoglobin multiparticulate. The present invention further provides a method for treating various diseases caused by oxygen deficiency comprising administering to a subject said enteric-coated hemoglobin multiparticulate in order to orally deliver the encapsulated hemoglobin-based oxygen carriers to a specific target of said subject in a controlled release manner.

19 Claims, 3 Drawing Sheets

(56) References Cited

OTHER PUBLICATIONS

Makhlof, A., et al. "Design and evaluation of novel pH-sensitive chitosan nanoparticles for oral insulin delivery." Eur J Pharm Sci., 2011, 42(5): 445-451.
Natanson, C., et al. "Cell-free hemoglobin-based blood substitutes and risk of myocardial infarction and death—A meta-analysis." J Amer. Med. Assoc., 2008, 299(19): 2304-2312.
Niederhofer, A., et al. "A method for direct preparation of chitosan with low molecular weight from fungi." Eur J Pharm Biopharm, 2004, 57: 101-105.
Paralikar, Swapnil J., et al. "High-altitude medicine." Indian J Occup Environ Med., 2010, 14(1): 6-12.
Remy, B., et al., "Red blood cell substitutes: fluorocarbon emulsions and hemoglobin emulsions." British Medical Bulletin, 1999, 55: 277-298.
Richard, A., et al. "Poly(glutamic acid) for biomedical applications." Crit Rev Biotechnol, 2001, 21: 219-232.
Sonaje, K., et al. "Enteric-coated capsules filled with freeze-dried chitosan/poly(gamma-glutamic acid) nanoparticles for oral insulin delivery." Biomaterials, 2010, 31(12): 3384-3394.
Sudarshan, N., et al. "Antibacteri action of chitosn." Food Biotechnology, 1992, 6(3): 257-272.
Baek et al. "Hemoglobin-driven pathophysiology is an in vivo consequence of the red blood cell storage lesion that can be attenuated in guinea pigs by haptoglobin therapy." The Journal of Clinical Investigation, 2012, 122(4): 1444-1458.
Becket, G., et al. "Improvement of the in vitro dissolution of praziquantel by complexation with $\alpha$-, $\beta$-, $\gamma$-cyclodextrins." International Journal of Pharmaceutics, 1999, 179(1): 65-71.
Blancher, C., et al. "Relationship of Hypoxia-inducible Factor (HIF)-1$\alpha$ and HIF-2$\alpha$ Expression to Vascular Endothelial Growth Factor Induction and Hypoxia Survival in Human Breast Cancer Cell Lines." Cancer Res., 2000, 60: 7106-113.
Gupta, V., et al. "A permeation enhancer for increasing transport of therapeutic macromolecules across the intestine." Journal of Controlled Release, 2013, 172(2): 541-549.
Honary, S., et al. "Effect of zeta potential on the properties of nano-drug delivery systems—a review (part 2)". Tropical Journal of Pharmaceutical Research, 2013, 12 (2): 263-273.
Yamamoto, A., et al. "Effects of various protease inhibitors on the intestinal absorption and degradation of insulin in rats." Pharmaceutical Research, 1994, 11(10): 1496-1500.
Derahkshadeh, K, et al. "In-vitro Cellular Uptake and Transport Study of 9-Nitrocamptothecin PLGA Nanoparticles Across Caco-2 Cell Monolayer Model." Iran J. Pharm. Res., 2011, 10(3): 425-434.

\* cited by examiner

ENTERIC-COATED HEMOGLOBIN MULTIPARTICULATE FOR ORAL DELIVERY OF HEMOGLOBIN BASED OXYGEN CARRIERS

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright© 2012-15, Billion King International Limited, All Rights Reserved.

TECHNICAL FIELD

The present invention relates to a process for making hemoglobin-based oxygen carrier (HBOC) containing pharmaceutical compositions suitable for oral delivery and the compositions produced thereby. The orally-deliverable HBOC compositions are suitable for treating a variety of conditions where enhanced tissue oxygenation is desirable.

BACKGROUND OF INVENTION

Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Since hemoglobin has this oxygen transport feature, it can be used as a potent oxygen supplier if it can be stabilized ex vivo and used in vivo.

Development of hemoglobin based oxygen carriers (HBOCs) has been pursued as an alternative to treatment with whole blood products. Typically, past HBOCs have been used as resuscitative fluids for hemorrhagic shock in emergency situations. However, there are various complications that have prevented widespread use of HBOCs. Such complications include extravasation of small-sized hemoglobin, myocardial infarction, hypertension, and renal toxicity (Bonaventura et al., 2007; Natanson et al., 2008). Various attempts to stabilize and purify the hemoglobin in HBOCs have yielded promising results; however, there is still no FDA-approved HBOC for routine clinical use.

While substantial research has been devoted to HBOC formulations for intravenous delivery, such intravenous delivery can be inconvenient or impossible in non-hospital settings. Therefore, there is a need in the art for HBOC compositions that can be delivered orally in non-hospital settings. Such compositions can be used to treat conditions where enhanced tissue oxygenation is desirable either due to medical or environmental conditions.

One environment where enhanced oxygenation is desirable is at high altitudes. High altitude syndrome (HAS) typically appears on rapid ascent to an altitude above 2,500 meters. Every day thousands of people travel to high altitudes, such as mountainous regions, and about 20% of them experience symptoms of HAS including headache, nausea, dizziness and sleep difficulty. Normally, the symptoms are sufficiently mild that they can be relieved by limiting activity and remaining at the same altitude for a few days for acclimatization. Without proper acclimatization and continuing to ascend, the sickness may progress to high altitude cerebral edema or high altitude pulmonary edema which is life threatening conditions that need to be treated aggressively (Paralikar, 2010).

Lower oxygen levels at high altitude increases ventilation by stimulating peripheral chemoreceptors, leading to hyperventilation. Hyperventilation reduces the alveolar carbon dioxide level, resulting in hypocapnia and alkalosis of blood. At the same time, cerebral blood flow increases to ensure adequate oxygen delivery. The resultant change in blood pH and the increase of cerebral pressure cause the mild symptoms described above. In response to the hypoxic environment, the human body initiates a series of adaptive mechanisms, i.e. acclimatization. For instance, the kidney excretes excessive bicarbonate and conserves hydrogen ions. Finally, blood and cerebrospinal fluid pH as well as ventilation rate are restored. Another important regulation is that hypoxia stimulates the release of the hormone erythropoietin from the kidney. Erythropoietin-sensitive committed stem cells in the bone marrow are stimulated to differentiate into red blood cells (RBC). New RBC can be generated and circulated in the blood stream within 4-5 days (Barrett et al., 2009). Long-term acclimatization leads to an increase in blood volume and RBC cell mass, therefore the oxygen-carrying capacity can be increased. Blood alkalosis shifts the oxygen-hemoglobin dissociation curve to the left. Meanwhile, a concomitant increase in RBC 2,3-diphosphoglycerate shifts the curve to the right. As a result, a net increase in p50 (affinity between hemoglobin and oxygen decreases) increases $O_2$ available to tissues (Barrett et al., 2009).

There have been various approaches taken in the past to treat HAS. Treatment with acetazolamide increases the rate of acclimatization (Paralikar, 2010). Acetazolamide, a renal carbonic anhydrase inhibitor, reduces bicarbonate re-absorption to maintain the balance of hydrogen ions. Moreover, acetazolamide inhibits cerebrospinal fluid production and reduces cerebrospinal fluid pressure. Steroids, particularly dexamethasone, have also been found to be effective in relieving symptoms (Hackett et al., 1988). However, both drugs (acetazolamide and steroids) are not targeting at enhancing cellular oxygen delivery to alleviate the condition. Additionally there have been reports that the Chinese herbal medicine *Rhodiola* can enhance blood oxygen levels (Xiu, 2002). However, there are side effects to *Rhodiola* including irritability, restlessness, and insomnia.

Regarding HBOCs, there have been some attempts to create alternative delivery mechanisms for the hemoglobin. One approach formulates hemoglobin-vesicles that mimic the cellular structure of RBC. Hemoglobin-vesicles are formed by encapsulating hemoglobin within a thin lipid bilayer membrane. However, such formulations, as with prior art HBOCs, are designed for intravenous delivery.

Oral drug delivery is convenient for patients, particularly in non-clinical settings; however several potential problems need to be solved, especially for protein-based drugs such as HBOCs. First, peptides or proteins can be degraded and digested by low pH gastric medium in the stomach and proteases in pancreatic juice. Second, the absorption of peptides or proteins in the intestine is hindered by their high molecular weight and hydrophilicity. Thus there is a need in the art for oral delivery HBOC compositions to ensure safe and effective delivery of oxygen to patients having a need for enhanced oxygen transport. Such a composition could be used to treat patients having HAS or other hypoxic conditions including blood loss, anemia, hypoxic cancerous tissue, and other oxygen-deprivation-based disorders.

U.S. Pat. No. 9,066,933 provided an oral delivery system for orally administering hemoglobin-based oxygen carrier to a subject in need thereof, said system comprises one or more nanoparticle solution, enteric-coated capsule, and/or enteric-coated tablet form(s). However, its efficiency in delivering said oxygen carrier via oral administration and absorption along the intestinal tract is not satisfactory according to some other studies. The size of the nanoparticles in 933 nm is too large (particles size>900 nm in diameter), which is difficult for transporting through gastrointestinal barriers by both paracellular passage (for particles size<50 nm) and endocytotic uptake (for particles size<500 nm) mechanism. (Derahkshadeh et al., 2011).

Therefore, an improved oral delivery system with higher efficiency in delivery hemoglobin-based oxygen carrier to a subject in needs thereof is therefore urgently needed.

SUMMARY OF INVENTION

The present invention provides an improved oral delivery system for delivering hemoglobin-based oxygen carrier more effectively to a subject in needs thereof, processes for making said system, and method for preventing and immediately treating high altitude syndrome (HAS), hypoxic conditions and other oxygen-deprivation disorders comprising using said system. Said delivery system, in particular, is an enteric-coated hemoglobin multiparticulate.

In a first aspect of the present invention, the enteric-coated hemoglobin multiparticulate comprises a core, a hemoglobin coating on top of the core, an inner coating or sub-coating, and an enteric coating. In one embodiment, said core is a starch pellet core. Similar materials that have equivalent properties can be used to make the core of the mutliparticulate of the present invention. In another embodiment, said core has a diameter of about 300 μm. In other embodiment, said hemoglobin coating is formed by spray coating of a formulation comprising hemoglobin-based oxygen carrier and other components. Said formulation comprises sucrose and hydroxypropyl-β-cyclodextrin (HPβCD) as stabilizers. In one embodiment, the inner coating or sub-coating of the multiparticulate comprises hydroxypropyl methylcellulose (HPMC). In another embodiment, the enteric coating of the multiparticulate comprises EUDRAGIT® L30 D-55, Triethyl citrate and Talc.

In a second aspect of the present invention, a method of preparing the enteric-coated hemoglobin multiparticulate in the first aspect is provided. The method comprises the following steps: providing a core; providing a hemoglobin formulation and coating thereof onto the surface of the core by spray coating to form a hemoglobin formulation coating; forming an inner or sub-coating onto the surface of the hemoglobin formulation coating by spray coating; forming an enteric coating onto the surface of the inner or sub-coating by spray coating. The present method is carried out at room temperature and atmospheric pressure, except the spray coating step which is carried out at higher temperature and pressure. In one embodiment, inlet air temperature of 45-50° C. is used during spray coating at a pressure of about 1.5 bar. Spray rate can range from 2 to 3 g/min. The desirable product temperature is kept at 35-36° C.

DETAILED DESCRIPTION OF INVENTION

The present invention is directed to an improved oral delivery formulations for HBOCs which deliver oxygen to the vasculature via oral administration. In an embodiment, enteric-coated hemoglobin multiparticulates are provided for effectively delivering the hemoglobin-based oxygen carrier to a specific site. Said enteric-coated hemoglobin multiparticulates are administered via oral administration. The hemoglobin-based oxygen carrier may include but not limited to purified hemoglobin, cross-linked hemoglobin, non-polymeric tetrameric hemoglobin, polymeric hemoglobin, and conjugated hemoglobin of various molecular weights. Examples of hemoglobin that can be used in the oral pharmaceutical compositions of the present invention are set forth in U.S. Pat. Nos. 7,932,356, 7,989,593, 8,048,856, 8,084,581, 8,106,011, the disclosures of which are incorporated by reference herein.

Figure 1:
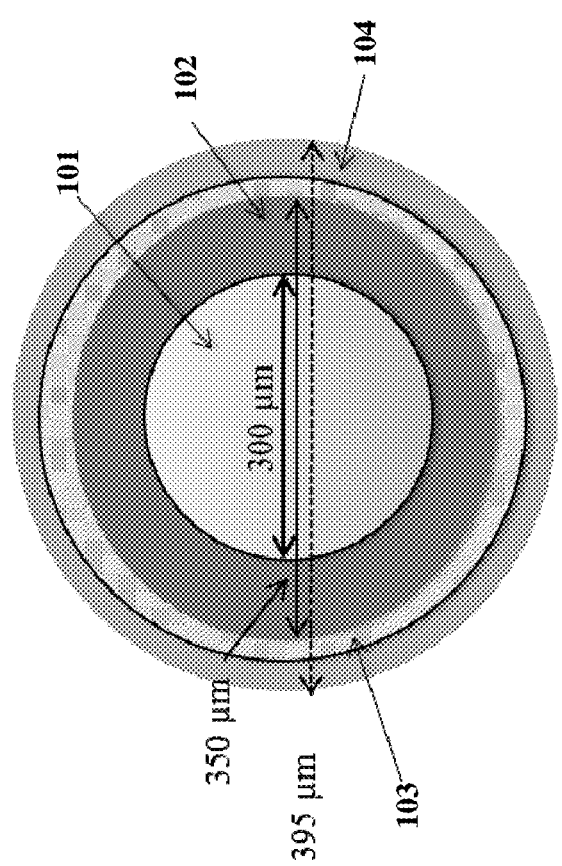
FIG. 1 shows the structure of enteric-coated hemoglobin multiparticulate.

FIG. 1 is a schematic diagram showing the structure of two-layer enteric-coated hemoglobin spray-dried encapsulated multiparticulate. Hemoglobin encaupsulated multiparticulates are prepared by Mini-Glatt Fluid Bed System. Fluidized bed coater was invented by Dr. D. Wurster at 1959, and it is applied in the field of pharmaceutical industry [U.S. Pat. No. 2,799,241]. The advantage of this method is to result in uniform coatings within a short operating time and with large-scale production. In this example, 10 g/dL bovine hemoglobin with 6% w/v sucrose and 4% w/v HPβCD in a hemoglobin formulation (or 26.3% w/w of the multiparticulate) (102) is sprayed on top of the starch pellet core (101) (43.7% w/w to total weight of the multiparticulate), followed by coating a layer of inner/sub-coating (103) comprising 10% w/w hydroxypropyl methylcellulose (HPMC), and a layer of enteric coating (104) (20% w/w to total weight of the multiparticulate) comprising 12.5% w/v EUDRAGIT® L30 D-55, 1.25% w/v Triethyl citrate and 6.25% w/v Talc, with the size of the multiparticulate of about 395 μm in diameter. Inside the multiparticulate, the diameter of the core is about 300 μm and the diameter of the spray-dried hemoglobin on top of the starch pellet core (or hemoglobin pellet) is about 350 μm.

Surcose and hydroxypropyl-β-cyclodextrin (HPβCD) are added into the present multiparticulate as stabilizer and cyroprotectant, while N-acetyl cysteine can serve as an antioxidant or an alternative to sucrose. HPβCD is a cyclic oligosaccharide with 7-membered sugar ring molecule. This molecule is approved by FDA as an oral drug stabilizer, and is commonly used in pharmaceutical applications for drug delivery. Its spatial arrangement of toroid structure (hydrophobic inside and hydrophilic outside) allows it to penetrate body tissues and forms complexes with hydrophobic pharmaceutical active ingredients. Thus, this stabilizer, HPβCD, enhances the solubility and bioavailability of the active ingredients (Becket et al., 1999).

Release study of the multiparticulates is performed in the simulated gastric fluid (pH 1.2 HCl solution, without pepsin) and the simulated intestinal fluid (pH 6.8 PBS solution, without pancreatin) at 37° C. Multiparticulate (0.05 g/mL) is placed into 50 mL of dissolution medium in two scenarios under peddle stiffing speed at 100 rpm: (1) acidic stage: simulated gastric fluid for 2 hours; (2) buffer stage: simulated intestinal fluid for 5 hours. Amount of hemoglobin released at different sampling time is determined by HPLC-UV measurement at 410 nm: (1) 2 mL of simulated gastric medium is aliquot in every 30 minutes, for hemoglobin quantitative analysis; (2) 2 mL of simulated intestinal fluid is aliquot at each 15 minutes (during the $1^{st}$ hour), or at each hour (from the $2^{nd}$ to $5^{th}$ hour).

Figure 2:
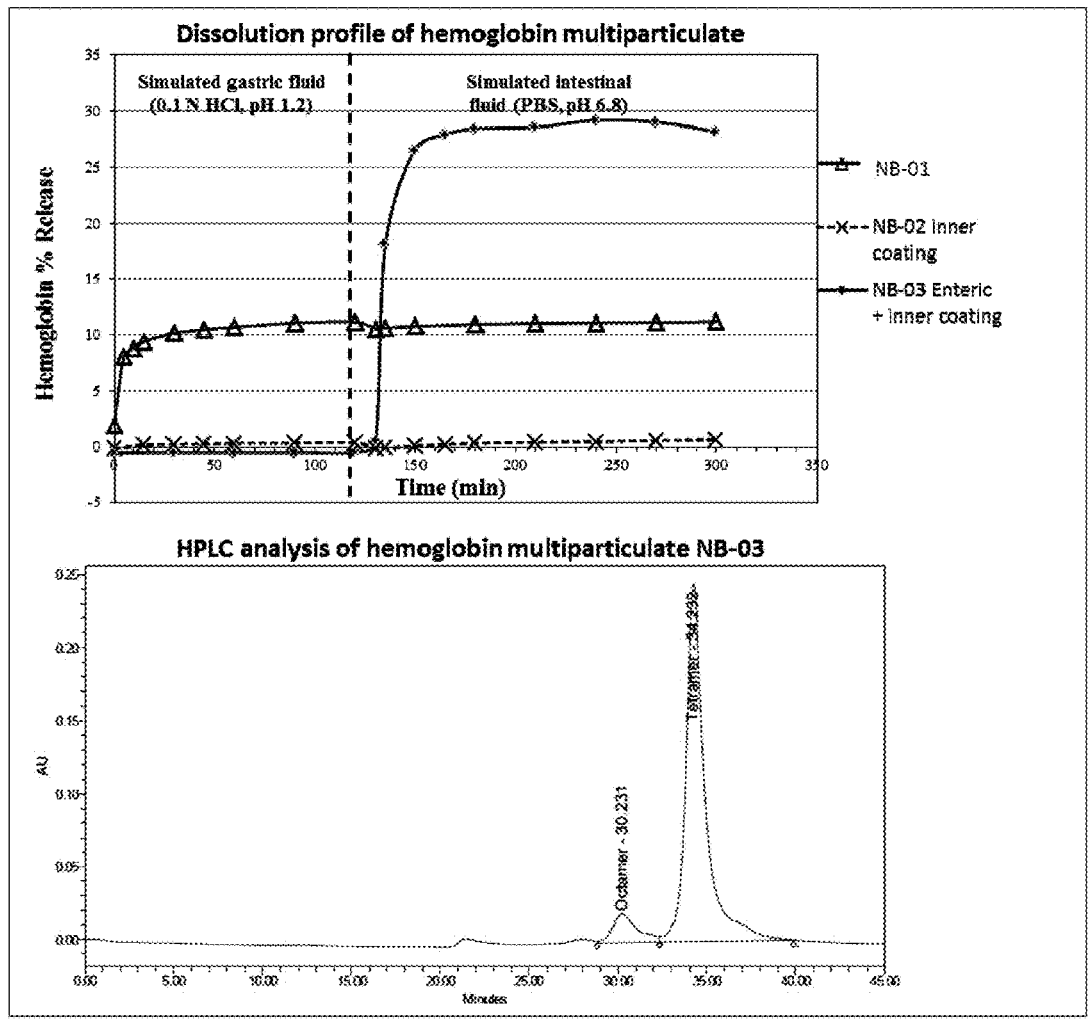
FIG. 2 shows the dissolution profiles and HPLC analysis of enteric-coated hemoglobin multiparticulates in simulated gastric fluid and simulated intestinal fluid.

In the hemoglobin quantitative measurement of dissolution test, the release of hemoglobin from the multiparticulates is compared with the one in hemoglobin pellet without enteric coating (NB-01) and pellet with one-layer inner coating (NB-02) (FIG. 2). For the multiparticulates without enteric coating (NB-01), it is seen that 12% of hemoglobin releases in pH 1.2 dissolution HCl solution at 37° C. within two hours, whereas no hemoglobin releases from both one-layer inner coating multiparticulates (NB-02) and enteric-coated multiparticulates (NB-03) in the simulating gastric fluid. It indicates that the enteric coating of the multiparticulates can well-protect the hemoglobin in the acidic simulated gastric fluid. At the same time, the enteric-coated multiparticulates (NB-03) has more satisfy hemoglobin release in simulated intestinal fluid (30% hemoglobin released), to compare with the one without coating (NB-01) (12% hemoglobin released) and with one-layer inner coating (NB-02) (0% hemoglobin released). HPLC result also supports the presence of hemoglobin tetramer in the simulated intestinal fluid mixed with enteric-coated multiparticulates (NB-03) for 2 hours.

Figure 3:
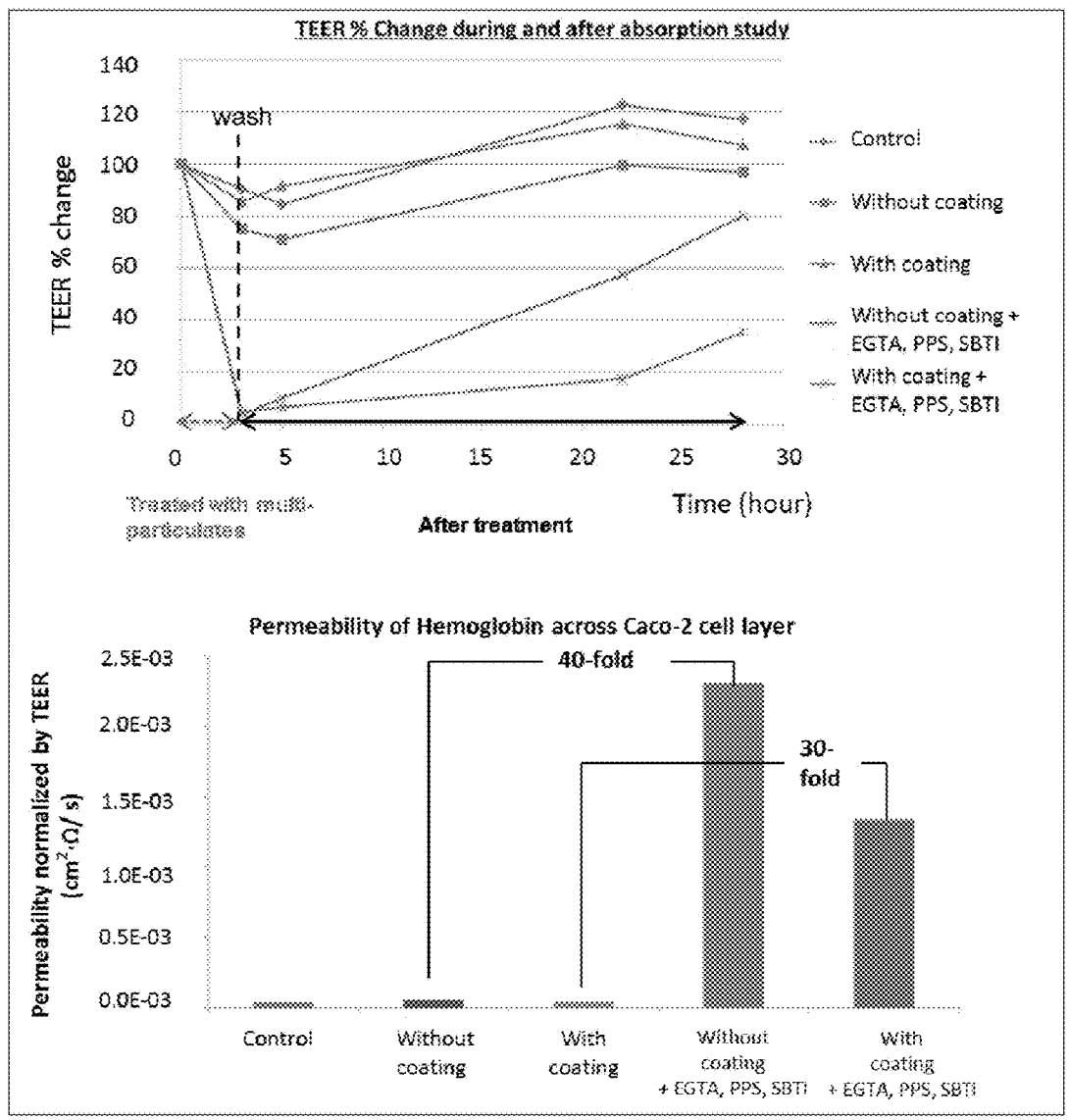
FIG. 3 TEER change and permeability of enteric-coated hemoglobin multiparticulates across Caco-2 cell layer.

TEER of hemoglobin enteric-coated multiparticulates is studied by using the Caco-2 cells monolayer trans-well culturing setup. Caco-2 cell culture model, which is culture of the human epithelial colorectal adenocarcinoma cell line, is a well-recognized method to the study of human intestine function and thereby drug intestinal absorption mechanism. Firstly, Caco-2 cells are grown in the T75 flask. DMEM (high glucose, Gibco) supplemented with 10% Fetal bovine serum (FBS), 1% Non-essential amino acids (NEAA), and antibiotics (50 U/ml penicillin and 50 µg/ml streptomycin) is used as the culture medium. The grown Caco-2 cells are trypsinized and $6×10^5$ cells are seeded onto each well of the tissue-culture treated polycarbonate Costar Trans-well 6 wells/plates (growth area 4.7 $cm^2$, Corning Costar Corp., N.Y.). The Caco-2 monolayer culture is kept in an atmosphere of 95% air and 5% $CO_2$ at 37° C. The medium is replaced every other day in the both apical and basolateral compartments. Millicell-Electrical Resistance System (Millipore Corp.) connected to a pair of chopstick electrodes is used to monitor the transepithelial electric resistance (TEER) which reveals the tightness of the tight junction between cells. The Caco-2 monolayer culture is used for the trans-epithelial transport study 19-21 days after seeding. The difference in TEER between the blank and the cell monolayer should be in the range of 400 ohm/$cm^2$ to 500 ohm/$cm^2$. The cells are fed with fresh medium 24 hours prior to the trans-epithelial transport study. Hemoglobin encapsulated multiparticulates with or without enteric coating, additional absorption enhancers (e.g. EGTA and PPS) and soybeans trypsin inhibitor (e.g. SBTI) is optionally loaded into the apical compartment. In one embodiment, 70 mg/mL EGTA, 4.5 mg/mL PPS, and/or 25 mg/mL SBTI can be loaded into the apical compartment. In another embodiment, 100 mg/mL of EGTA and 4.5 mg/mL of PPS can be loaded. Cells are incubated at 37° C. with orbital shaking at 50 r.p.m. for 3 hours after the loading. The initial and time point TEER values are measured. FIG. 3 shows the result that TEER values rebounded after treating with multiparticulates alone, which indicates that the multipaticulates are not invasive. After the experiment, 2 mL of HBSS at the basolateral compartment are collected for the permeability measurement by HPLC analysis. The permeability is calculated by comparing the amount of multiparticulates in the basolateral compartment at the end and the initial multiparticulates amount in the apical compartment. A 30-fold (with enteric coating) and 40-fold (without enteric coating) enhancement of hemoglobin encapsulated multiparticulates permeability is achieved by the addition of EGTA, PPS and SBTI (FIG. 3). It is confirmed that the hemoglobin encapsulated multiparticulates can be absorbed with the presence of absorption enhancers and protease inhibitors.

Compared to intravenous delivery of peptides or proteins, oral delivery has an advantage in pharmacokinetics because an oral delivery system enables controlled release of peptide or protein from the carriers. Such a controlled release mode of delivery of peptide or protein drug is unavailable in direct intravenous delivery. For hemoglobin being introduced into the vascular system, a controlled release and sustained elevation of the hemoglobin concentration in the blood has a greater physiological benefit than that from a sudden substantial increase of free hemoglobin in the injection site from direct injection. A rapid increase in the hemoglobin level increases the chance of developing side effects such as extravasation, myocardial infarction and renal toxicity.

The heme group of hemoglobin in HBOC consists of an iron (Fe) ion (charged atom) held in a heterocyclic ring. In addition to delivering oxygen to the human body by HBOC, the heme group can provide heme iron to the body to aid in the production of more red blood cells. Acetazolamide, steroids and *Rhodiola* cannot provide heme iron to the body.

Oral delivery of HBOCs is a non-invasive, convenient and efficient way to prevent or treat HAS, and therefore, it is favorable for people to take before or during travel from a sea level region to a high altitude region. Absorption of undegraded hemoglobin in intestinal tract, skipping de novo synthesis of hemoglobin, increases the oxygen-carrying capacity of blood thus increasing the rate of acclimatization. The orally-deliverable HBOCs can also be used to treat acute anemia due to blood loss or to prepare individuals for physically-demanding activities in normal or low oxygen supply atmosphere, e.g. for athletes, astronauts, divers, or navy personnel stationed in submarines. Improving tissue oxygenation by HBOCs is further useful for preventing/treating tissue ischemia, and promotes wound healing, such as diabetic foot ulcers. While the foregoing invention has been described with respect to various embodiments, such embodiments are not limiting. Numerous variations and modifications would be understood by those of ordinary skill in the art. Such variations and modifications are considered to be included within the scope of the following claims.

The following references relate to various aspects of the present invention and are incorporated by reference herein:

Artursson, P., et al. "Effect of chitosan on the permeability of monolayers of intestinal epithelial cells (Caco-2)." *Pharm Res.*, 1994, 11: 1358-1361.

Baek et al. "Hemoglobin-driven pathophysiology is an in vivo consequence of the red blood cell storage lesion that can be attenuated in guinea pigs by haptoglobin therapy." *The Journal of Clinical Investigation*, 2012, 122(4): 1444-1458.

Ballard, T. S., et al. "Regulation of tight-junction permeability during nutrient absorption across the intestinal epithelium." *Annu. Rev. Nutr*, 1995, 15: 35-55.

Barnikol, W. K., et al. "Complete healing of chronic wounds of a lower leg with haemoglobin spray and regeneration of an accompanying severe dermatoliposclerosis with intermittent normobaric oxygen inhalation (INBOI): a case report." *Ger Med Sci.,* 2011, 9 (DOI: 10.3205/000131).

Barrett, K. E., et al. "New Delhi: Tata-McGraw-Hill." *Ganong's Review of Medical Physiology,* 2009, 23$^{rd}$ edition, pp. 619-20.

Becket, G., et al. "Improvement of the in vitro dissolution of praziquantel by complexation with α-, β-, γ-cyclodextrins." *International Journal of Pharmaceutics,* 1999, 179(1): 65-71.

Blancher, C., et al. "Relationship of Hypoxia-inducible Factor (HIF)-1α and HIF-2α Expression to Vascular Endothelial Growth Factor Induction and Hypoxia Survival in Human Breast Cancer Cell Lines." *Cancer Res.,* 2000, 60: 7106-113.

Bonaventura, C., et al. "Allosteric effects on oxidative and nitrosative reactions of cell-free hemoglobin." *IUBMB Life,* 2007, 59(8-9): 498-505.

Brunel, F., et al. "Self-assemblies on chitosan nanohydrogels." *Macromol Biosci.,* 2010, 10(4): 424-432.

Cicco, G., et al. "Wound healing in diabetes: hemorheological and microcirculatory aspects." *Adv Exp Med Biol.* 2011, 701: 263-269.

Derahkshadeh, K., et al. "In-vitro Cellular Uptake and Transport Study of 9-Nitrocamptothecin PLGA Nanoparticles Across Caco-2 Cell Monolayer Model." *Iran J. Pharm. Res.,* 2011, 10(3): 425-434.

Dünnhaupt, et al. "Distribution of thiolated mucoadhesive nanoparticles on intestinal mucosa." *International Journal of Pharmaceutics,* 2011, 408 (1-2): 191-199

Gupta, V., et al. "A permeation enhancer for increasing transport of therapeutic macromolecules across the intestine." *Journal of Controlled Release,* 2013, 172(2): 541-549.

Hackett, P. H., et al. "Dexamethasone for prevention and treatment of acute mountain sickness." *Aviat space Environ Med.,* 1988, 59: 950-954.

Hiromi, Sakai, et al. "Review of Hemoglobin-Vesicles as Artificial Oxygen Carriers." *Artificial organs,* 2009, 33(2): 139-145.

Honary, S., et al. "Effect of zeta potential on the properties of nano-drug delivery systems—a review (part 2)". *Tropical Journal of Pharmaceutical Research,* 2013, 12 (2): 263-273

Iwasaki, N, et al. "Feasibility of polysaccharide hybrid materials for scaffolds in cartilage tissue engineering: evaluation of chondrocyte adhesion to polyion complex fibers prepared from alginate and chitosan." *Biomacromolecules,* 2004, 5(3): 828-833.

Levien, L. J. "South Africa: clinical experience with Hemopure." *ISBT Science Series,* 2006, 1(1): 167-173.

Lin, Y. H., et al. "Multi-ion-crosslinked nanoparticles with pH-responsive characteristics for oral delivery of protein drugs." *J Control Release.,* 2008: 132(2), 141-149.

Makhlof, A., et al. "Design and evaluation of novel pH-sensitive chitosan nanoparticles for oral insulin delivery." *Eur J Pharm Sci.,* 2011, 42(5): 445-451.

Natanson, C., et al. "Cell-free hemoglobin-based blood substitutes and risk of myocardial infarction and death—A meta-analysis." *J Amer. Med. Assoc.,* 2008, 299(19): 2304-2312.

Niederhofer, A., et al. "A method for direct preparation of chitosan with low molecular weight from fungi." *Eur J Pharm Biopharm,* 2004, 57: 101-105.

Paralikar, Swapnil J., et al. "High-altitude medicine." *Indian J Occup Environ Med.,* 2010, 14(1): 6-12.

Remy, B., et al., "Red blood cell substitutes: fluorocarbon emulsions and hemoglobin emulsions." *British Medical Bulletin,* 1999, 55: 277-298.

Richard, A., et al. "Poly(glutamic acid) for biomedical applications." *Crit Rev Biotechnol,* 2001, 21: 219-232.

Sonaje, K., et al. 'Enteric-coated capsules filled with freeze-dried chitosan/poly(gamma-glutamic acid) nanoparticles for oral insulin delivery." *Biomaterials,* 2010, 31(12): 3384-3394.

Sudarshan, N., et al. "Antibacteri action of chitosn." *Food Biotechnology,* 1992, 6(3): 257-272.

Wong, B. L., et al. (2011), U.S. Pat. Nos. 7,932,356, 7,989,593, 8,048,856 & 8,084,581

Wong, B. L., et al. (2012), U.S. Pat. No. 8,106,011

Wong, B. L., et al. (2015), U.S. Pat. No. 9,066,933

Xiu, R. (2002), U.S. Pat. No. 6,399,116

Yamamoto, A., et al. "Effects of various protease inhibitors on the intestinal absorption and degradation of insulin in rats." *Pharmaceutical Research,* 1994, 11(10): 1496-1500.

What is claimed is:

1. An enteric-coated hemoglobin multiparticulate for oral delivery of hemoglobin-based oxygen carrier to a subject in need thereof, said multiparticulate comprising a core, a hemoglobin formulation coating surrounding said core, wherein said hemoglobin formulation comprises ethylene glycol tetraacetic acid and palmitoyl dimethyl ammonio propane-sulfonate, an inner or sub-coating surrounding said hemoglobin formulation coating, and an enteric coating surrounding said inner or sub-coating, wherein said ethylene glycol tetraacetic acid and palmitoyl dimethyl ammonio propane-sulfonate are present at a concentration of 100 mg/mL and 4.5 mg/mL, respectively, in said hemoglobin formulation.

2. The multiparticulate of claim 1, wherein said core is made of starch to form a starch pellet core.

3. The multiparticualte of claim 1, wherein said hemoglobin formulation further comprises hemoglobin-based oxygen carriers, one or more stabilizers, and an aqueous solution.

4. The multiparticulate of claim 1, wherein said inner or sub-coating comprises hydroxypropyl methylcellulose.

5. The multiparticulate of claim 1, wherein said enteric coating comprises poly(methyacrylic acid-co-ethyl acrylate) 1:1, Triethyl citrate and Talc.

6. The multiparticulate of claim 3, wherein said hemoglobin formulation further comprises a protease inhibitor.

7. The multiparticulate of claim 3, wherein said hemoglobin-based oxygen carriers are at a concentration of 10 g/dL in said hemoglobin formulation.

8. The multiparticulate of claim 3, wherein said one or more stabilizers comprise 6% w/v sucrose and 4% w/v hydroxypropyl-β-cyclodextrin in said hemoglobin formulation.

9. The mutliparticulate of claim 6, wherein said protease inhibitor comprises soybean trypsin inhibitor at 25 mg/mL in said hemoglobin formulation.

10. The multiparticulate of claim 1, wherein said core has a weight percentage of 43.7% w/w to total weight of said multiparticulate.

11. The multiparticulate of claim 1, wherein said hemoglobin formulation coating has a weight percentage of 26.3% w/w to total weight of said multiparticulate.

12. The multiparticulate of claim 1, wherein said inner or sub-coating has a weight percentage of 10% w/w to total weight of said multiparticulate.

13. The multiparticulate of claim 1, wherein said enteric coating has a weight percentage of 20% w/w to total weight of said multiparticulate.

14. The multiparticulate of claim 1, wherein said mutliparticulate has an average size of about 395 µm.

15. A method of preparing the multiparticulate of claim 1 comprising:
   a) Providing a core;
   b) Providing a hemoglobin formulation comprising ethylene glycol tetraacetic acid and palmitoyl dimethyl ammonio propane-sulfonate;
   c) Coating said hemoglobin formulation on said core by spray coating to form a hemoglobin formulation coating surrounding said core;
   d) Coating a solution of hydroxypropyl methylcellulose on said hemoglobin formulation coating by spray coating to form an inner or sub-coating surrounding said hemoglobin formulation coating;
   e) Coating on said inner or sub-coating with an enteric coating by spray coating.

16. The method of claim 15, wherein said core is a starch pellet core.

17. The method of claim 15, wherein said hemoglobin formulation comprises a hemoglobin-based oxygen carriers at 10 g/dL, 6% w/v sucrose and 4% w/v hydroxypropyl-β-cyclodextrin.

18. The method of claim 17, wherein said hemoglobin formulation comprises 100 mg/mL ethylene glycol tetraacetic acid, 4.5 mg/mL palmitoyl dimethyl ammonio propanesulfonate and further 25 mg/mL soybean trypsin inhibitor.

19. The method of claim 15, wherein said enteric coating comprises 12.5% w/v poly(methyacrylic acid-co-ethyl acrylate) 1:1, 1.25% w/v Triethyl citrate and 6.25% w/v Talc.

* * * * *